(12) United States Patent
Stevenson

(10) Patent No.: US 10,226,635 B2
(45) Date of Patent: Mar. 12, 2019

(54) TOROIDAL COMPRESSIBLE ELEMENT INCLUDING A SWITCHBACK PATTERN

(71) Applicant: Cardiac Pacemakers, Inc., St. Paul, MN (US)

(72) Inventor: Mark Stevenson, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 203 days.

(21) Appl. No.: 15/079,071

(22) Filed: Mar. 24, 2016

(65) Prior Publication Data

US 2016/0199655 A1  Jul. 14, 2016

Related U.S. Application Data

(62) Division of application No. 13/722,952, filed on Dec. 20, 2012, now Pat. No. 9,308,380.

(60) Provisional application No. 61/580,725, filed on Dec. 28, 2011.

(51) Int. Cl.
| | | |
|---|---|---|
| *A61N 1/37* | (2006.01) | |
| *A61N 1/375* | (2006.01) | |
| *H01R 13/187* | (2006.01) | |
| *H01R 43/16* | (2006.01) | |

(52) U.S. Cl.
CPC ......... *A61N 1/3754* (2013.01); *A61N 1/3752* (2013.01); *H01R 13/187* (2013.01); *H01R 43/16* (2013.01)

(58) Field of Classification Search
CPC .. A61N 1/3752; A61N 1/3758; A61N 1/3968; H01R 43/16

USPC ................................. 607/2, 36, 37
See application file for complete search history.

(56) References Cited

U.S. PATENT DOCUMENTS

| | | | |
|---|---|---|---|
| 4,469,104 A | 9/1984 | Peers-Trevarton | |
| 4,934,367 A | 6/1990 | Daglow et al. | |
| 5,076,270 A | 12/1991 | Stutz, Jr. | |
| 5,545,842 A | 8/1996 | Balsells | |
| 5,556,414 A * | 9/1996 | Turi ......................... | A61F 2/07 606/198 |
| 5,575,487 A | 11/1996 | Balsells | |
| 5,599,027 A | 2/1997 | Balsells | |
| 5,662,692 A | 9/1997 | Paspa et al. | |
| 5,769,671 A | 6/1998 | Lim | |

(Continued)

FOREIGN PATENT DOCUMENTS

| | | |
|---|---|---|
| EP | 0339877 A2 | 11/1989 |
| EP | 2797668 B1 | 3/2017 |

(Continued)

OTHER PUBLICATIONS

"U.S. Appl. No. 13/722,952, Advisory Action dated Jul. 7, 2014", 3 pgs.

(Continued)

*Primary Examiner* — Christopher A Flory

(74) *Attorney, Agent, or Firm* — Schwegman Lundberg & Woessner, P.A.

(57) ABSTRACT

A method includes obtaining or providing a sheet of material; forming from the material a member comprising a plurality of switchback portions that zigzag about a loop; and shaping the member such that the plurality of switchback portions are elastically deformable and zigzag and curve about the loop.

12 Claims, 14 Drawing Sheets

(56) References Cited

U.S. PATENT DOCUMENTS

| | | | |
|---|---|---|---|
| 6,098,989 | A | 8/2000 | Caplain et al. |
| 6,749,358 | B2 | 6/2004 | Balsells |
| 7,003,351 | B2 | 2/2006 | Tvaska et al. |
| 7,031,774 | B1 | 4/2006 | Doan et al. |
| 7,070,455 | B2 | 7/2006 | Balsells |
| 7,164,951 | B2 | 1/2007 | Ries |
| 7,195,523 | B2 | 3/2007 | Naviaux |
| 7,274,964 | B2 | 9/2007 | Balsells |
| 7,299,095 | B1 | 11/2007 | Barlow et al. |
| 7,316,593 | B2 | 1/2008 | Balsells |
| 7,467,013 | B2 | 12/2008 | Tvaska et al. |
| 7,722,415 | B2 | 5/2010 | Chansrivong |
| 7,822,477 | B2 | 10/2010 | Rey et al. |
| 7,890,175 | B1 | 2/2011 | Rey et al. |
| 7,914,351 | B2 | 3/2011 | Balsells et al. |
| 7,955,145 | B2 | 6/2011 | Chansrivong |
| 8,052,459 | B2 * | 11/2011 | Smith .................. A61N 1/3752 439/372 |
| 8,078,280 | B2 | 12/2011 | Sage et al. |
| 8,091,226 | B2 * | 1/2012 | Sjostedt .............. A61N 1/3752 29/874 |
| 8,096,838 | B2 * | 1/2012 | Dilmaghanian ..... A61N 1/3752 439/669 |
| 8,244,357 | B2 | 8/2012 | Tvaska et al. |
| 8,282,429 | B2 * | 10/2012 | Glick ................... H01R 13/187 439/843 |
| 8,328,587 | B2 * | 12/2012 | Dilmaghanian ....... H01R 24/58 439/827 |
| 8,342,893 | B2 * | 1/2013 | Glick ................... H01R 13/187 439/840 |
| 8,366,475 | B2 * | 2/2013 | Smith .................. A61N 1/3752 439/372 |
| 8,428,724 | B2 | 4/2013 | Sage |
| 8,430,698 | B2 * | 4/2013 | Stewart ................ H01R 13/187 439/843 |
| 8,437,855 | B2 * | 5/2013 | Sjostedt .................. A61N 1/05 29/876 |
| 8,500,499 | B2 * | 8/2013 | Drew .................. A61N 1/3752 439/843 |
| 8,666,494 | B2 * | 3/2014 | Schramm ............. A61N 1/3752 607/37 |
| 8,761,887 | B2 * | 6/2014 | Schramm ............. A61N 1/3752 607/37 |
| 9,308,380 | B2 * | 4/2016 | Stevenson ............ A61N 1/3754 |
| 2005/0107859 | A1 | 5/2005 | Daglow et al. |
| 2005/0228480 | A1 * | 10/2005 | Douglas .................... A61F 2/07 623/1.13 |
| 2006/0004419 | A1 | 1/2006 | Olbertz |
| 2006/0058832 | A1 * | 3/2006 | Melzer ..................... A61F 2/01 606/200 |
| 2007/0207186 | A1 * | 9/2007 | Scanlon .................... A61F 2/07 424/424 |
| 2008/0255631 | A1 * | 10/2008 | Sjostedt ............... A61N 1/3752 607/37 |
| 2008/0262628 | A1 * | 10/2008 | Laitenberger ............. A61F 2/91 623/23.7 |
| 2009/0048638 | A1 * | 2/2009 | Rey ...................... A61N 1/3752 607/37 |
| 2009/0233491 | A1 | 9/2009 | Barker et al. |
| 2010/0197174 | A1 | 8/2010 | Lahti et al. |
| 2010/0204780 | A1 * | 8/2010 | Fliedner .................... A61F 2/91 623/1.16 |
| 2011/0022102 | A1 * | 1/2011 | Rey ...................... A61N 1/3752 607/2 |
| 2013/0172949 | A1 | 7/2013 | Stevenson |
| 2013/0253638 | A1 * | 9/2013 | Douglas .................... A61F 2/07 623/1.46 |

FOREIGN PATENT DOCUMENTS

| | | |
|---|---|---|
| JP | 2002532135 A | 10/2002 |
| JP | 2015503401 A | 2/2015 |
| WO | WO-2013101683 A1 | 7/2013 |

OTHER PUBLICATIONS

"U.S. Appl. No. 13/722,952, Advisory Action dated Jul. 29, 2015", 3 pgs.

"U.S. Appl. No. 13/722,952, Final Office Action dated Apr. 23, 2014", 7 pgs.

"U.S. Appl. No. 13/722,952, Final Office Action dated May 21, 2015", 9 pgs.

"U.S. Appl. No. 13/722,952, Non Final Office Action dated Jan. 10, 2014", 8 pgs.

"U.S. Appl. No. 13/722,952, Non Final Office Action dated Feb. 5, 2015", 7 pgs.

"U.S. Appl. No. 13/722,952, Notice of Allowance dated Dec. 11, 2015", 7 pgs.

"U.S. Appl. No. 13/722,952, Response filed Apr. 10, 2014 to Non Final Office Action dated Jan. 10, 2014", 8 pgs.

"U.S. Appl. No. 13/722,952, Response filed May 5, 2015 to Non Final Office Action dated Feb. 5, 2015", 7 pgs.

"U.S. Appl. No. 13/722,952, Response filed Jul. 21, 2015 to Final Office Action dated May 21, 2015", 7 pgs.

"U.S. Appl. No. 13/722,952, Response filed Jul. 23, 2014 to Advisory Action dated Jul. 7, 2014", 7 pgs.

"U.S. Appl. No. 13/722,952, Response filed Dec. 17, 2013 to Restriction Requirement dated Nov. 21, 2013", 6 pgs.

"U.S. Appl. No. 13/722,952, Restriction Requirement dated Nov. 21, 2013", 7 pgs.

"Australian Application Serial No. 2012362623, Subsequent Examiners Report dated Mar. 3, 2015", 4 pgs.

"International Application Serial No. PCT/US2012/071073, International Preliminary Report on Patentability dated Jul. 10, 2014", 5 pgs.

"International Application Serial No. PCT/US2012/071073, International Search Report dated Mar. 25, 2013", 3 pgs.

"International Application Serial No. PCT/US2012/071073, Written Opinion dated Mar. 25, 2013", 3 pgs.

"Japanese Application Serial No. 2014-550388, Office Action dated Jun. 9, 2015", with English translation, 6 pgs.

* cited by examiner

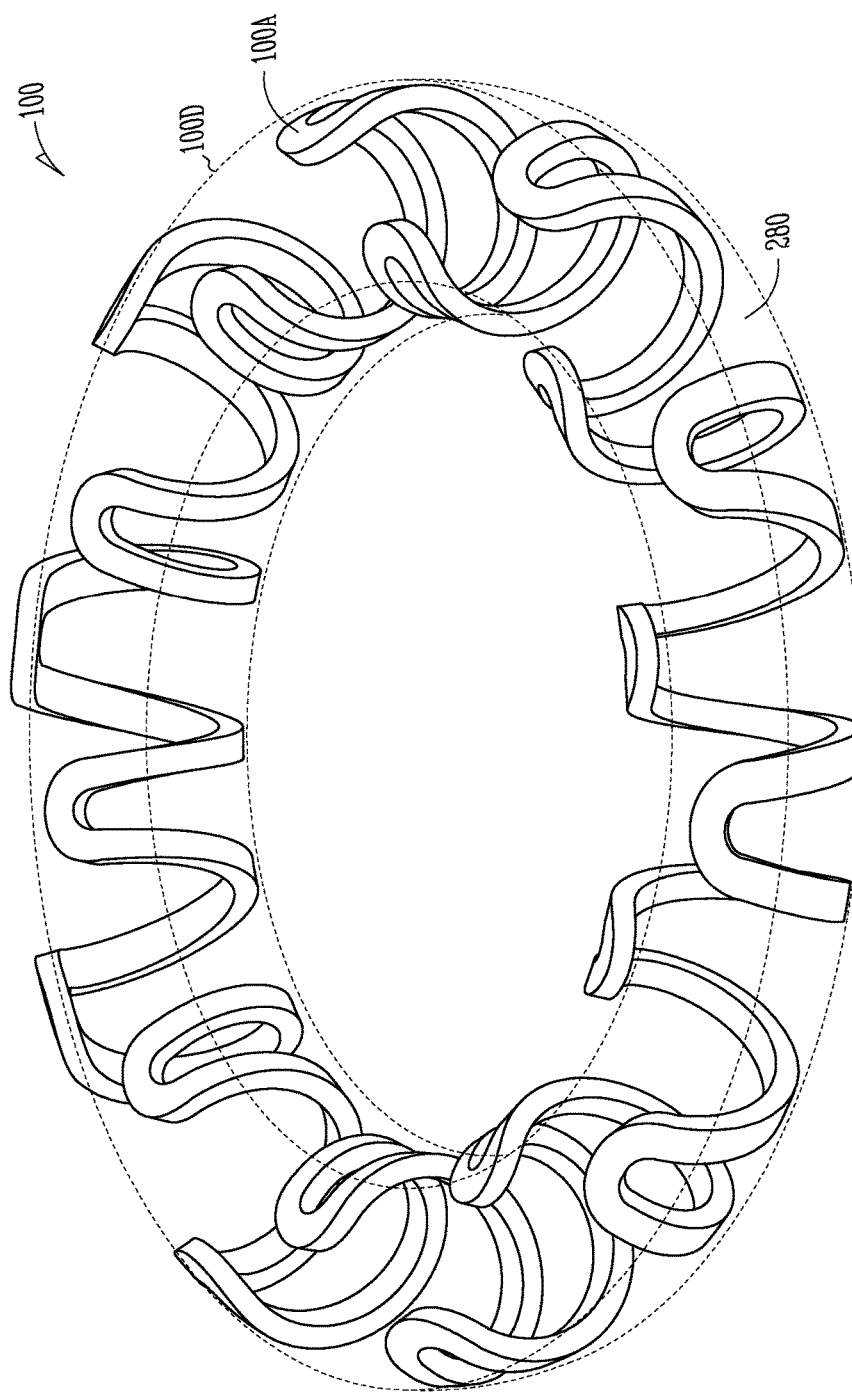

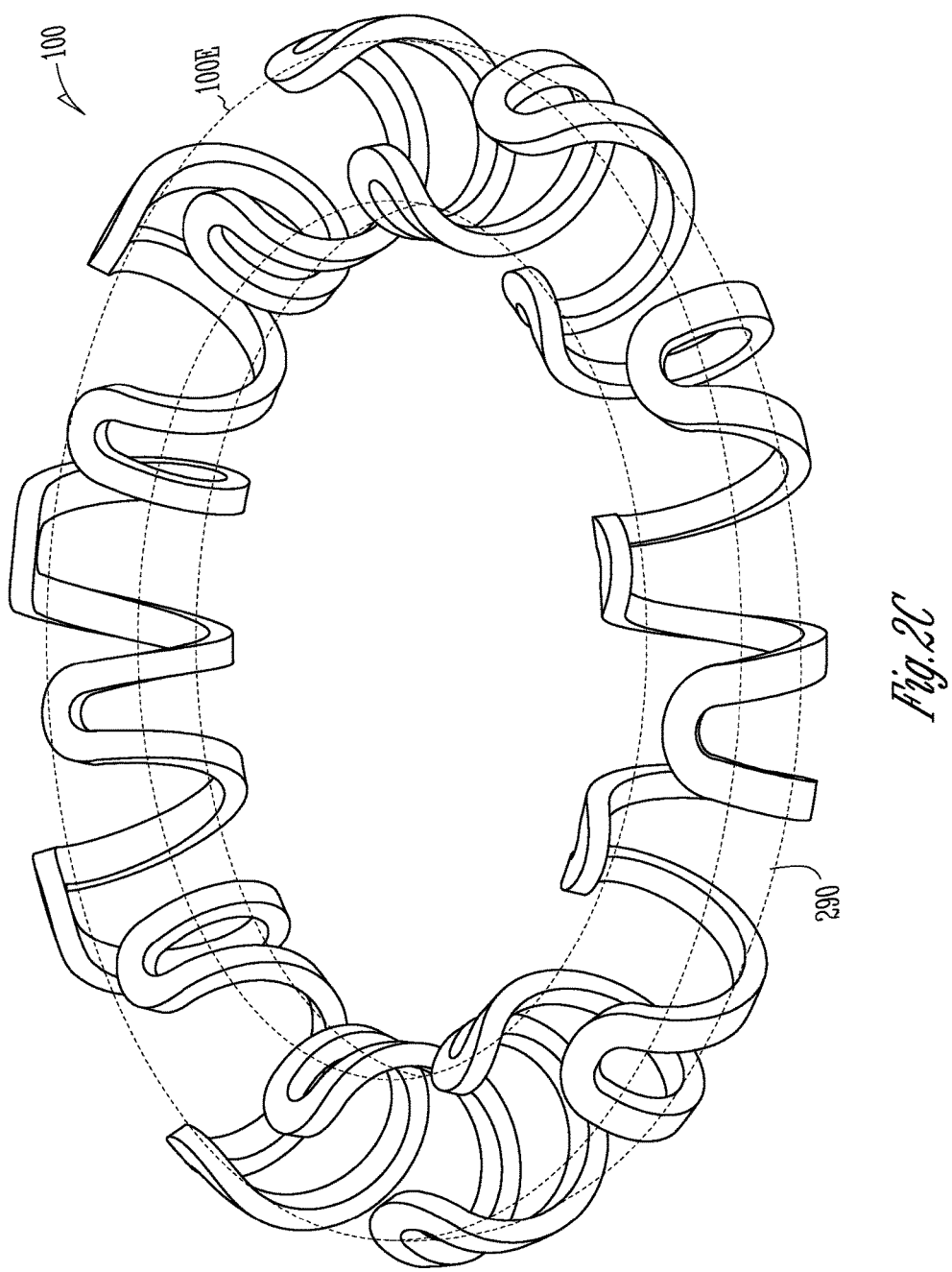

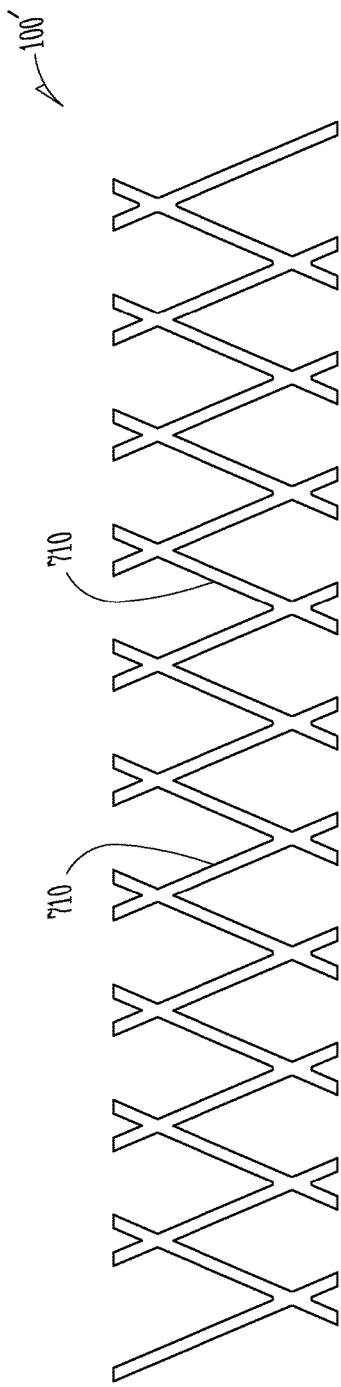
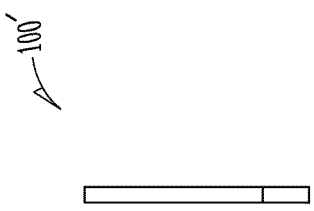
Fig. 7A
Fig. 7B

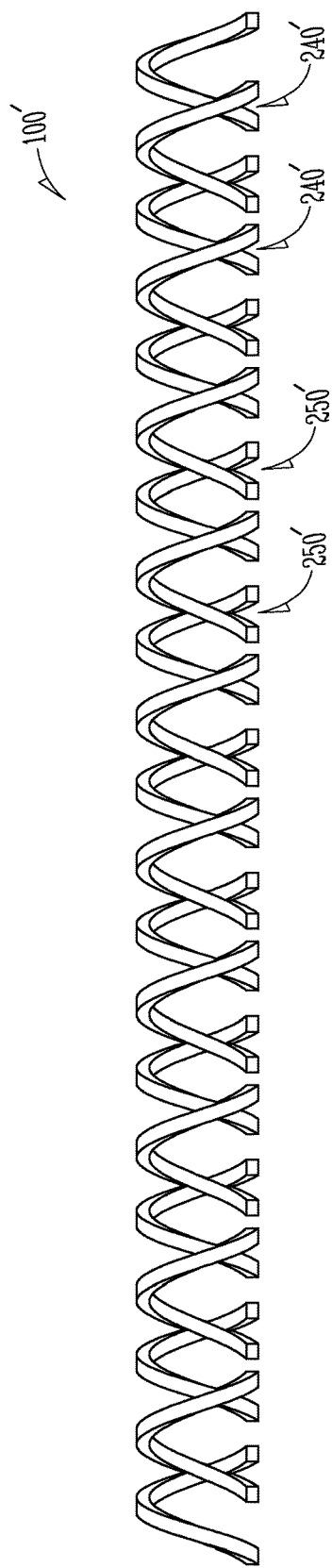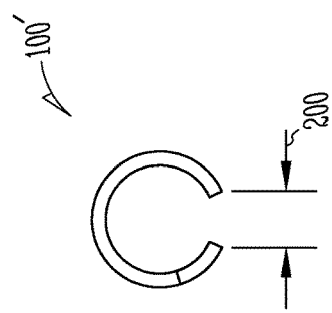
Fig. 8A
Fig. 8B

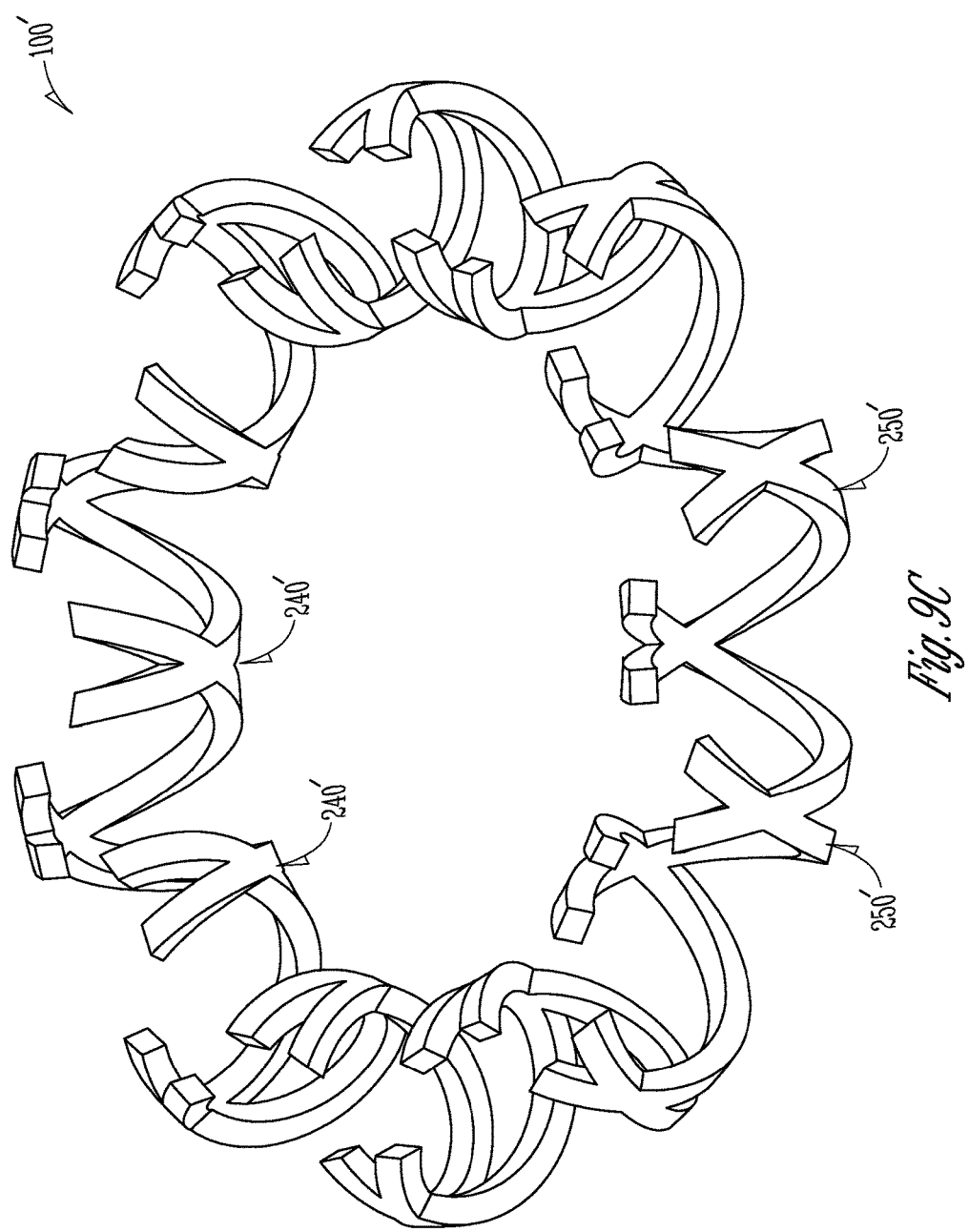

US 10,226,635 B2

TOROIDAL COMPRESSIBLE ELEMENT INCLUDING A SWITCHBACK PATTERN

CLAIM OF PRIORITY

This application is a division of U.S. application Ser. No. 13/722,952, filed Dec. 20, 2012, now issued as U.S. Pat. No. 9,308,380, which claims the benefit of priority under 35 U.S.C. § 119(e) of Stevenson, U.S. Provisional Patent Application Ser. No. 61/580,725, entitled "TOROIDAL COMPRESSIBLE ELEMENT INCLUDING A SWITCHBACK PATTERN", filed on Dec. 28, 2011, each of which is herein incorporated by reference in its entirety.

BACKGROUND

A connector, for example a medical device connector, can benefit from features that can form, and reform, robust connections, including physical and electrical connections. For implantable medical devices, including, but not limited to, pacemakers, defibrillators, or neurostimulators, it can be important to provide a physical and electrical connection to a lead carrying an electrode. Examples of electrodes include an electrical stimulation electrode and a sensing electrode.

BRIEF DESCRIPTION OF THE DRAWINGS

The drawings are not necessarily drawn to scale. The drawings illustrate generally, by way of example, but not by way of limitation, various embodiments discussed in the present document.

FIG. 2B is a perspective view of the spring of FIG. 2A disposed in a conceptual toroid.

FIG. 2C is a perspective view of the spring of FIG. 2A with a conceptual toroid confined within the inner void of the spring.

FIG. 7A shows a top view of an example of the spring in a planar state, according to an example.

FIG. 7B shows a side view of the spring of FIG. 7A in a planar state.

FIG. 8A shows a top view of the spring apparatus in a rolled state, according to an example.

FIG. 8B shows a side view of the spring of FIG. 8A in a rolled state.

FIG. 9C is a perspective view of an example of the spring of FIG. 9A.

FIG. 10 is an example of a method of creating a spring, according to an example.

FIG. 11 is an example of a method of creating a spring, according to an example.

DETAILED DESCRIPTION

Figure 1A:
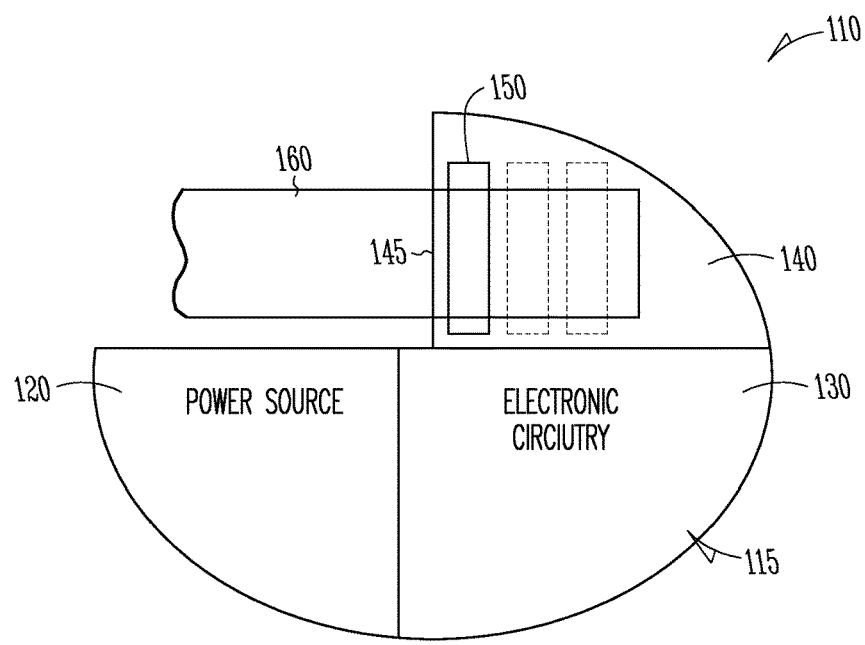
FIG. 1A shows a front view of an implantable medical device, according to an example.

FIG. 1A shows a front view of an example of an implantable medical device 110. The implantable medical device 110 can be sized or shaped or otherwise configured to be implanted inside a subject, to electrostimulate or otherwise provide electrical energy to the subject's heart or elsewhere. The implantable medical device 110 can include an electronics unit 115. The electronics unit 115 can include one or more of the following: a power source 120, electronic circuitry 130, and a header 140. The electronics unit 115 can define one or more recesses inside a spring retainer 150, the one or more recesses sized to receive a spring, as discussed herein. The illustration shows one spring retainer 150, and two optional spring housings, drawn in broken line.

Figure 1B:
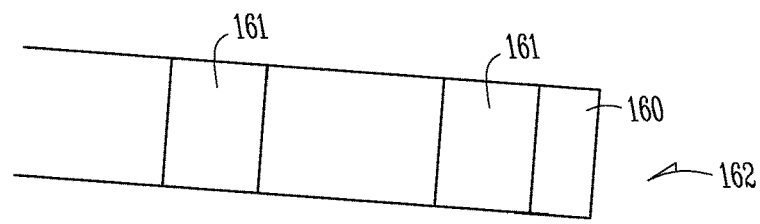
FIG. 1B shows a front view of the lead of FIG. 1A, showing multiple electrical contacts.
Figure 1C:
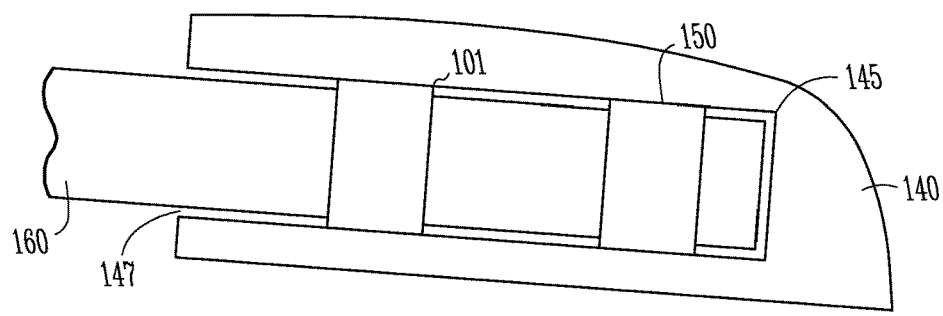
FIG. 1C shows a front view of the lead of FIG. 1A, coupled to a header of an implantable medical device.

FIG. 1B shows a front view of a lead 160 with two electrical contacts 161. The electronics unit 115 of the implantable medical device 110 can be coupled to the lead 160, through a header 140, in an example. FIG. 1C shows a front view of a lead 160 with multiple electrical contacts 161 coupled to and paired with contacts disposed in the header 140 of an implantable medical device 110. The header 140 can be hermetically sealed to a housing that retains electronic circuitry 130.

The lead 160 can be sized or shaped or otherwise configured to extend through a subject, for example intravascularly. When implanted, the lead can extend from a proximal end at the header 140 of the implantable medical device 110 to a distal end, located at a target region. Examples of target regions include, but are not limited to, a subject's heart, nerves or nerve bundles, and the like. The lead 160 can provide one or more electrodes at a target region. One or more electrodes can be used to sense an electrical signal or other physiological parameter from the target region or to deliver electrical energy from the implantable medical device 110.

The lead 160 can be coupled to the header 140 of the implantable medical device 110, to create one or more electrical contacts between the lead 160 and the electronics unit 115 of the implantable medical device 110. An electrical contact in the header 140, for example one or more of the springs discussed herein, can be at least electrically connected to a wire, trace, or other conductor routed into the hermetically-sealed electronics unit 115 of the implantable medical device 110, to communicate an electrical signal between the electronics unit 115 and the lead 160. The springs discussed herein can be physically coupled to such a conductor, through welding, soldering and the like.

A header 140 can include multiple spring housings. A spring housing 150 can contain one or more contacts to make electrical contact with electrical contacts of the lead 160, through a conductive spring. In an example, each spring retainer retains a conductive, substantially annular spring 100, for example the spring 100 shown in FIG. 2A. In turn, each spring retainer includes a contact that is in electrical communication with other electronics inside the electronics unit 115. Therefore, each spring 100 can provide an electrical contact between the implantable medical device 110 and the lead 160. More than one spring can establish physical and electrical contact with the lead 160. The spring retainers 150 can extend circumferentially about the lead bore receptacle 145, to encircle the lead 160 when the lead 160 is located in the lead bore receptacle 145.

The header 140 can be molded or otherwise formed to define the spring retainer 150. The header can be formed by disposing a resin into a mold. The spring retainer can be excised into the header. The header can then be insert-molded around the preformed spring retainer. An insert can define one or more spring retainers 150 and the insert can include one or more springs 100, such that a spring 100 is disposed in each spring retainer 150. The header 140 can be configured to accept the insert, to allow the insert to be coupled to the header 140, through a pressing operation in which the insert is interference fit into the header 140.

As shown in FIG. 1C, the header 140 can include a lead bore receptacle 145, that defines an opening 147 sized to receive a proximal end 162 of the lead 160, to dispose the lead 160 into the header 140. The header 140 can optionally include more than one lead bore receptacle 145, to couple more than one lead 160 to the implantable medical device 110. In some embodiments, the lead 160 can define a lead form factor shaped to conform to an interior form factor of the lead bore receptacle 145. In additional examples, the lead bore receptacle 145 can be defined in part by the one or more spring retainers 150. The lead bore receptacle 145 can include multiple spring retainers 150 that can be spaced-apart, to match the positions of the electrical contacts 101 of the lead 160, for example while the lead 160 is coupled to the header 140. Multiple springs 100, each disposed by a spring retainer 150, can collectively create multiple physical and electrical interconnections with the lead 160.

Various examples reduce the complexity of such interconnections. A less complex connection between an implantable medical device electronics unit and an electrode-carrying lead can decrease surgery time. Examples can improve reliability, at least because they provide redundant electrical connection points. Examples also decrease instances of spring breakage, because they stress the spring more lightly by distributing a load among several contact points, and by deforming contact points less.

Figure 2A:
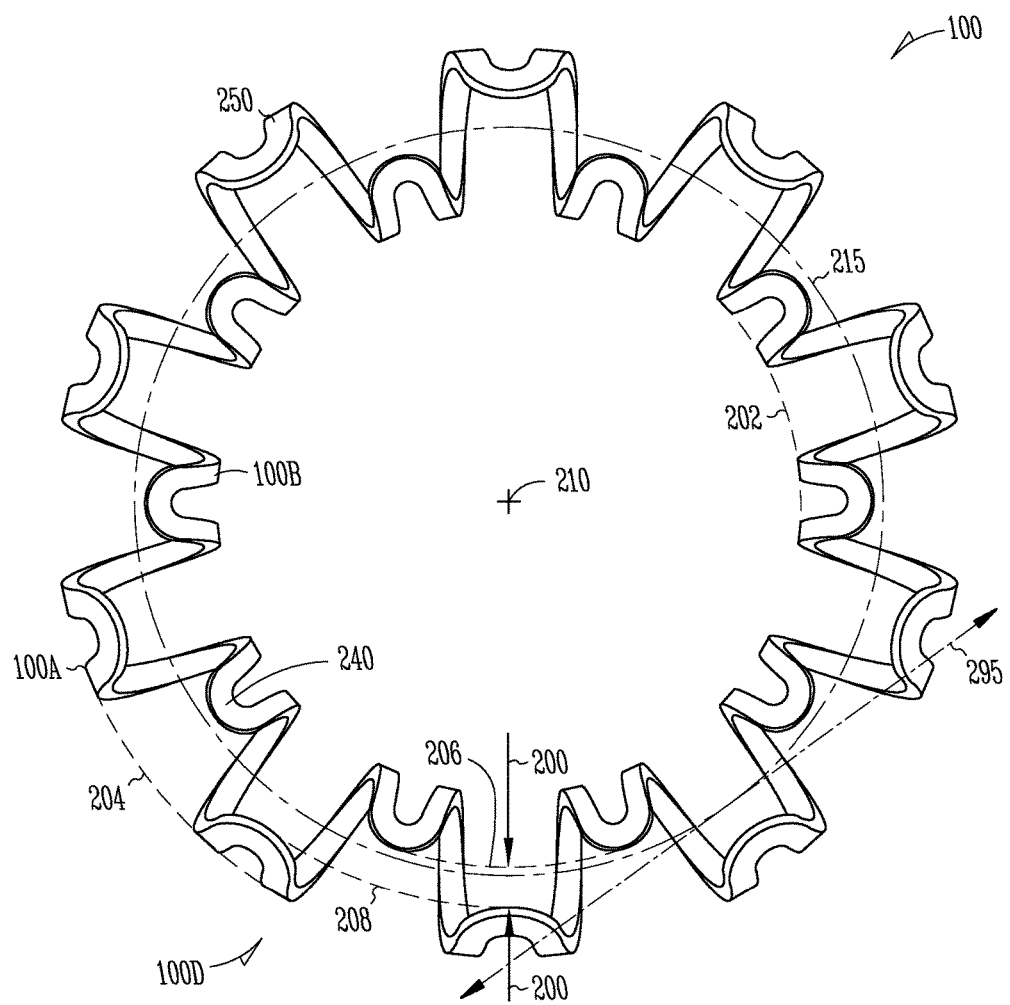
FIG. 2A is a perspective view of the spring with switchback portions that zigzag and curve transversely about a loop, according to an example.

FIG. 2A is a perspective view of an example of a substantially annular or substantially toroidal spring 100. In an example, the spring 100 extends along a conceptualized annulus or loop (i.e., a loop-shaped datum or reference) 215. The loop 215 can be substantially circular. In other examples, the loop 215 can be asymmetrical about a plane including the centerline 210.

The spring 100 can be formed to define a constant distance between the centerline 210 and an inner circumference 202 of the spring 100. The spring can also define a constant distance between the centerline 210 and an outer circumference 204 of the spring 100. An inner circumference 202 of the spring can be at least partially defined by one or more portions of the spring 100 that are closest to the centerline 210. A part of each inner switchback portion 240 that is closest to the centerline 210 can define the inner circumference 202. The spring is configured to make multiple mechanical and electrical contacts along the inner circumference. By providing multiple contacts, redundancy is increased. Multiple contacts also distribute stress better than single contact designs, which can decrease breakage due to stressing the spring. Multiple contacts designs additionally allow lead mating at a larger angle away from the centerline 210 of the bore.

An outer circumference 204 can be at least partially defined by one or more portions of the spring 100 that are farthest from the centerline 210 and on the same plane as the inner circumference 202, for example the part of each outer switchback portion 250 that is farthest from the centerline 210. The distance between an inner circumference 202 and the centerline 210 can vary along the path of the loop 215. The distance between the outer circumference 204 and the centerline 210 can vary along the path of the loop 215.

FIG. 2B is a perspective view of the spring 100, the outer surface 100A of individual elements 100B defining a portion of a conceptualized outer toroidal surface 280 (i.e., an outer reference surface), for example a ring torus. The spring 100 can fit within the conceptualized outer toroidal surface 280.

FIG. 2C is a perspective view of a spring 100, showing an interior void 100E defined by the spring 100. In an example, the interior void 100E can define a portion of a conceptualized inner toroidal surface 290 (i.e., an inner reference surface), for example a ring torus. The conceptualized inner toroidal surface 290 can fit within the interior void 100E of the spring 100.

Space between the individual elements 100B of the spring 100 can permit unobstructed access between the interior void 100E defined by the spring 100 and an exterior region 100D outside of the spring 100. The exterior region 100D includes the region extending from the conceptualized outer toroidal surface 280 away from the conceptualized inner toroidal surface 290.

The spring 100 can be continuous and monolithic. The ring-shape can be circular, extending around the centerline 210 at a constant distance. The ring-shape can be as asymmetrical about a plane including the centerline 210, with a first element (e.g., a switchback) on one side of the plane being a different distance from the centerline 210 than a second element opposite the first element about the plane. An asymmetrical shape can provide a shape that conforms to the outer periphery of a proximal end of the lead 160, when the proximal end of the lead 160 presents a matching asymmetrical shape.

The ring-shape can include a keyed portion to pair with a matching keyed portion of a spring retainer. Key or keyway features can inhibit or prevent rotation of the spring 100 inside a spring retainer. Such features can be defined by a portion of the loop 215 that departs from a regular shape defined by the remainder of the loop 215 (e.g., a circle or ellipses).

Individual elements 100B of the spring 100 can comprise switchback portions 240, 250 that zigzag. In an example, the switchback portions 240, 250 can zigzag about the conceptualized loop 215, around the conceptualized centerline 210. The switchback portions 240, 250 can curve transversely about the conceptualized loop 215, such that the switchback portions 240, 250 are transverse or crosswise to the loop and are curved around the conceptualized loop 215. In other words, a cross-section taken at a plane including the centerline 210 shows that the switchback portions curves along the cross-section. In some examples, only one of the switchback portions 240, 250 curve.

The switchback portions 240, 250 can extend transverse or crosswise to the loop, such that the switchback portions 240, 250 are normal to the conceptualized loop 215. The switchback portions 240, 250 can curve transversely about the conceptualized loop 215, so as to partially define the first conceptualized ring torus surface 280. For example, although the loop 215 need not extend through a plane, in instances where it does, the switchback portions 240, 250 can extend transverse to the plane, by extending orthonormal to the plane. In an example, a linear portion 260 can be curved around a conceptualized tangential axis 295 that extends tangential to the loop 215.

The spring 100 can define a loop-shaped gap 200 that can extend around the centerline 210. The gap 200 can allow access to the toroid-shaped interior void 100E from the exterior region 100D. The loop-shaped gap 200 can be defined between the inner switchback portions 240 and the outer switchback portions 250. The loop-shaped gap 200 can extend continuously around the centerline 210. The gap 200 can define a generally uniform width continuously around the centerline 210, such that the inner switchback portions 240 ends can be respectively located at a first generally uniform distance 206 from the centerline 210 and the outer switchback portions 250 ends can be respectively located at a second generally uniform distance 208 from the centerline 210. The gap 200 can be of a consistent size as it extends around the centerline 210. The gap 200 can extend around the spring 100, on one side of a plane that bisects the spring 100 perpendicular to the centerline 210. The loop-shaped gap 200 can be on a plane perpendicular to the centerline 210. In an example, the loop-shaped gap 200 can be located on the outside circumferential periphery (for example the outer circumference 204) of the spring 100. In an example, the loop-shaped gap 200 can be located on part of the ring between the top-most part of the spring 100 and the outer circumference 204 of the spring 100, for example at a 45° or other angle to the centerline 210. The loop-shaped gap 200 is optional; it does not need to be located along a planar side of the torus. In an example, switchbacks are interdigitated with one another.

The spring 100 is useful to locate the lead 160 into a lead receptacle at a desired orientation. In an example, the spring 100 can provide a detent mechanism, to mechanically resist translation of the lead 160 through a lead receptacle. In an example, a detent can engage the proximal end of the lead 160 to provide mechanical and electrical contact. The spring 100 can be elastically deformed in use. In an example, the spring 100 is compressed, reducing the diameter of the loop 215, by bending one or both of the switchback portions 240, 250 or linear portions extending between switchback portions.

To form an electrical connection with a contact on the lead 160, the spring 100 can be electrically conductive. Such conductivity can allow signal communication between the implantable medical device 110 and the lead 160. In an example, the spring 100 is formed of conductive material. In an example, the spring 100 is formed of non-conductive and conductive material, with conductive material contacting both the lead 160 and an electrical contact disposed in a spring retainer 150, with non-conductive material providing support, protection, or insulation around the conductive material. The spring 100 can be formed of the same material that forms at least part of the spring retainer 150. The spring 100 can include a biocompatible material, for example MP35N or stainless steel. In an example, MP35N can comprise 35% Ni, 35% Co, 20% Cr, and 10% Mo. MP35N is a federally registered trademark of SPS Technologies, LLC, with operations located at 301 Highland Ave., Jenkintown, Pa. 19046. The spring 100 can be formed from a single piece of material. The spring 100 can be age-treated, to strengthen the spring 100.

Figure 3A:
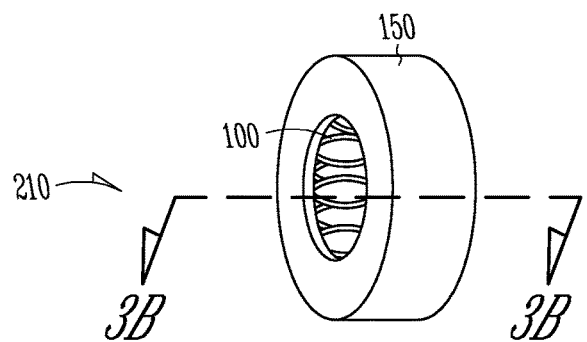
FIG. 3A is a perspective view of the spring inside a spring retainer, according to an example.

FIG. 3A is a perspective view of an example of the spring 100, located at least partially inside the spring retainer 150.

The inner profile of the spring retainer 150 can be of similar size as the outer profile of the spring 100, to at least partially constrain the spring 100 inside the spring retainer. The spring 100 can be at least partially constrained within the spring retainer 150 by having a physical connection with a boundary of the spring retainer 150, which restricts movement of the spring 100. The spring 100 can include a portion that extends beyond the spring retainer 150, into the lead bore receptacle 145. The spring 100 can protrude into the lead bore receptacle 145, to contact a corresponding electrical contact 161 on the proximal end of the lead 160 when the proximal end of the lead 160 is inserted into the lead bore receptacle 145.

Figure 3B:
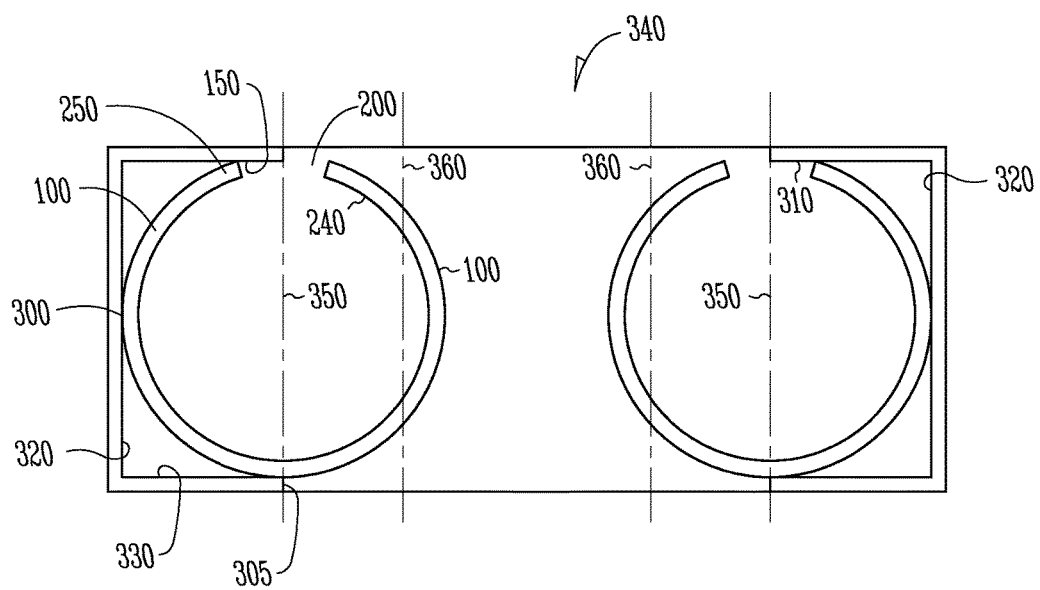
FIG. 3B shows a front view of a cross-section of the spring disposed in a spring retainer, taken along line 3B-3B in FIG. 3A.

FIG. 3B shows a front view of a cross-section of the spring 100 inside the spring retainer 150, taken at cross-section 3B-3B in FIG. 3A. The spring 100 can be at least partially constrained within the spring retainer 150. The spring 100 can abut the top surface 310 inside the spring retainer 150, the outer surface 320 inside the spring retainer 150, or the bottom surface 330 inside the spring retainer 150, to restrict movement of the spring 100. The spring retainer 150 can include an electrical contact 300. The electrical contact can be disposed along any surface inside the spring retainer. The electrical contact 300 can be sized and shaped such that the spring 100 can be seated against the electrical contact 300, to relay an electrical signal to or from a corresponding electrical contact 161 on the proximal end of the lead 160. The contact between the spring 100 and the spring retainer 150 can be a point contact. The spring retainer 150 can be connected to a wire, trace or other conductor that can be connected to the implantable medical device 110, to allow an electrical signal to travel to the implantable medical device 110 to the lead 160 or from the lead 160 to the implantable medical device 110.

The spring 100 can extend beyond (i.e. toward the centerline 210) the inner portion 305 of the spring retainer 150, to contact the lead 160. The inner portion 305 can terminate at axis 350, and the gap 200 can be exposed to the lead bore receptacle 145. The inner portion 305 can terminate at axis 360, such that the gap 200 is not exposed to the lead bore receptacle 145, to inhibit or prevent the lead 160 from catching the gap 200 of the spring 100 when the proximal end of the lead 160 is passed through center of the spring retainer 150 and the center lumen 340 of the spring 100 during installation. The inner portion 305 can terminate along other axes. The inner portion 305 of the top surface 310 can terminate at the same axis that the inner portion 305 of the bottom surface 330 terminates at, for example at axis 350. The inner portion 305 of the top surface 310 can terminate at a different axis than the inner portion 305 of the bottom surface 330 terminates at, for example the inner portion of the top surface 310 terminates at axis 350 and the inner portion 305 of the bottom surface 330 terminates at axis 360.

The proximal end of the lead 160 can extend along the lead bore receptacle 145 through the center lumen 340 encircled by the spring retainer 150 and through the center lumen 340 defined by the spring 100 along the conceptualized centerline 210. The lead 160 can compress the spring 100 in a radial direction against the spring retainer 150, for example when the lead 160 occupies a portion of the lead bore receptacle 145 that the spring 100 extends into, and this can provide electrical and mechanical contact between the spring 100 and the spring retainer 150.

Figure 4A:
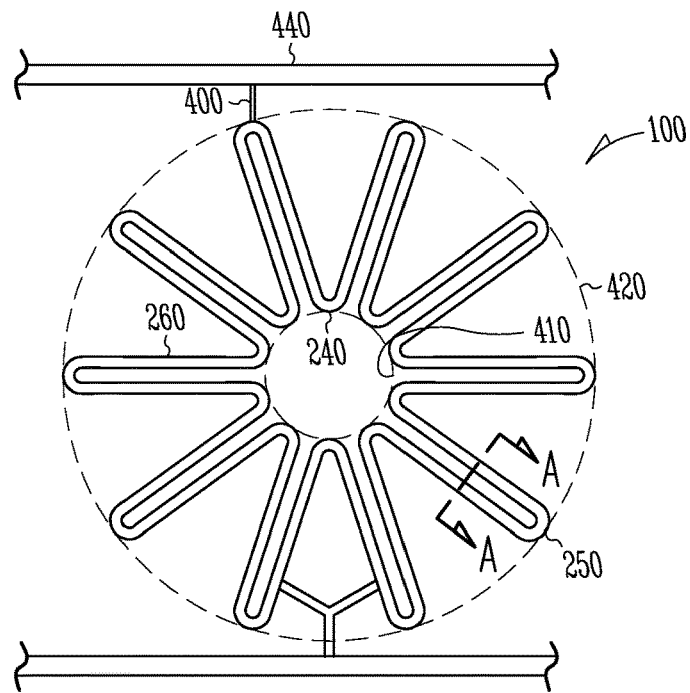
FIG. 4A shows a top view of the spring in a planar state with a web, according to an example.

FIG. 4A is top view of the spring 100 in a planar state coupled with a carrier member 400, according to an example. The spring 100 can exist in a planar state during the forming process or can enter the planar state by flattening a spring 100 for example the spring 100 shown in FIG. 2A. In a planar state the carrier member 400 can attach the spring 100 to the strip of material 440 the spring 100 was derived from. The carrier member 400 can connect the spring 100 to a strip of material 440, to assist in locating the spring 100 during manufacturing. The carrier member 400 can connect the spring 100 to a strip of material 440, to assist in restraining the spring 100 during the manufacturing process. The carrier member 400 can connect the spring 100 to a strip of material 440, to maintain a location of the spring 100 with respect to a fixture during the manufacturing process.

The manufacturing process can include stamping, to remove material and define the shape of the spring 100. The manufacturing process can include rolling, to create the spring 100 from a spring 100 in a planar state. The carrier member 400 can be the same material as the spring 100, for example when material is removed from a sheet of material to define the shape of the spring 100 and to define the carrier member 400. The carrier member 400 can comprise a residual material not removed during the process of forming the spring 100, created by stamping in an example.

The spring 100 can be created by progressive-die stamping a 2-dimensional pattern from a sheet of material. A pattern for a spring 100 in a planar state can be created by laser excising the shape from a sheet. The spring 100 can be created by machining the shape from a sheet of material, for example by removing material by cutting. Other forming processes are possible including, but not limited to, machining the spring 100 from billet, rapid prototyping the spring 100, casting the spring 100, etc.

Figure 9A:
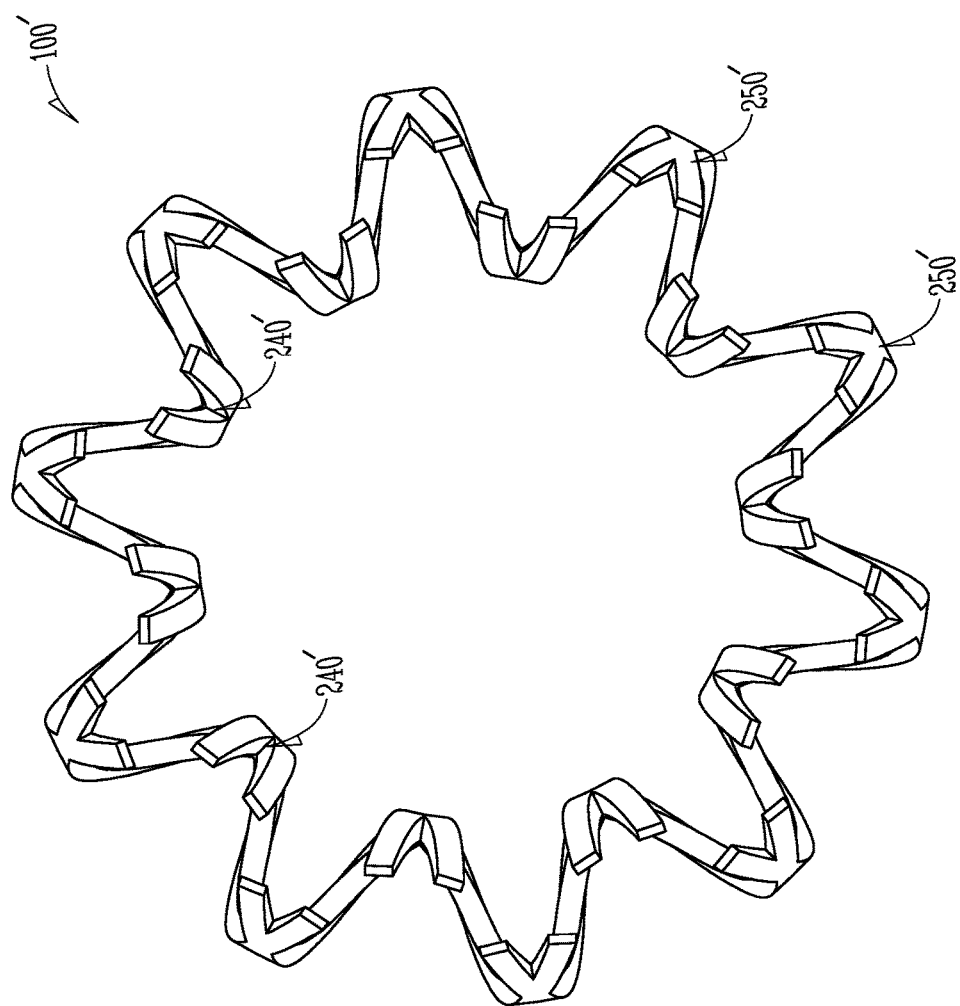
FIG. 9A shows a top view of an example of the spring, according to an example.
Figure 9B:
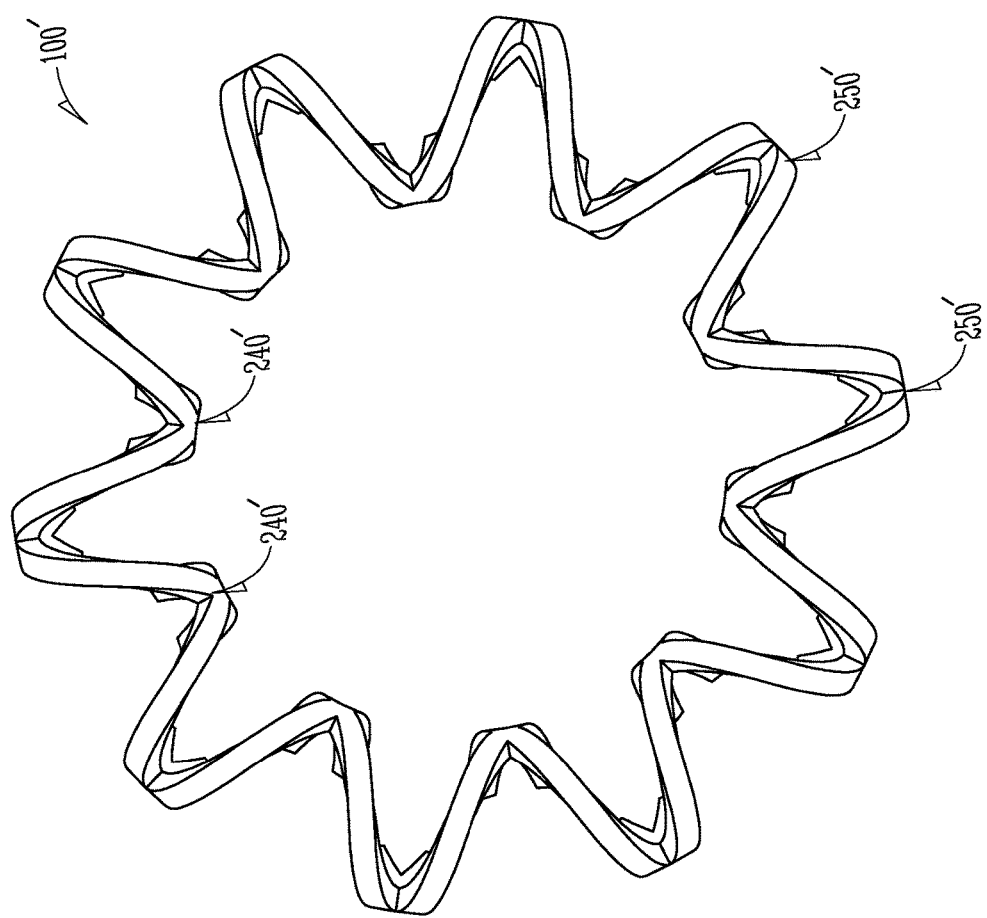
FIG. 9B is a bottom view of an example of the spring of FIG. 9A.

The spring 100 can include switchback portions 240, 250. In an example, the switchback portions 240, 250 can be arc-shaped (as shown in FIGS. 2A and 4A). In an example, the switchback portions 240, 250 can be "X" shaped (as shown in FIGS. 9A, 9B, and 9C). In an example, the switchback portions 240, 250 can form a vertex ending in a point. There can be inner switchback portions 240 and outer switchback portions 250. The inner switchback portions 240 can be connected to the outer switchback portions 250 by linear portions 260.

A cross-section of a switchback portion 240, 250 or linear portion 260, such the cross-section along line A-A, can be rectangular. The cross-section can be rectangular. Some stamped examples have a rectangular cross-section. The cross-section of a switchback portion 240, 250 or linear portion 260, along line A-A, can be circular, for example if the spring 100 is created from a wire with a circular cross-section. The switchback portions 240, 250 and the linear portions 260 can have the same characteristics, thickness and width. In an example, the width of the switchback portions 240, 250 and the linear portions 260 can be constant. In an example, the width of the switchback portions 240, 250 and the linear portions 260 can vary, to reinforce locations of higher stress. In an example, the thickness of the switchback portions 240, 250 and the linear portions 260 can be constant. In an example, the thickness of the switchback portions 240, 250 and the linear portions 260 can vary, to reinforce locations of higher stress. The ratio between thickness and width can be 1:1, 1:2, 2:1, 2:3, or 3:2. Other ratios between the thickness and the width are possible.

In an example where the spring 100 is in a planar state, the inner switchback portions 240 can define a first circumference 410 of the spring 100 and the outer switchback portions 250 can define a second circumference 420 of the spring 100. Linear portions 260 can extend between the first circumference 410 and the second circumference 420. The first circumference 410 can be smaller than the second circumference 420, to define the inner portion of the spring 100 and the outer portion of the spring 100. The first circumference 410 and the second circumference 420 can be conceptual elements. The first circumference 410 and the second circumference 420 can define a portion of a circle or a loop.

Figure 4B:
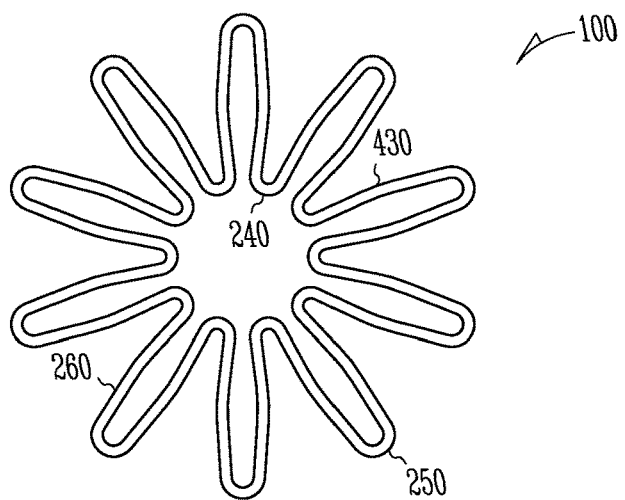
FIG. 4B shows a top view of the spring of FIG. 4A, shown in a planar state with bends in linear portions.

FIG. 4B shows a top view of the spring 100 in a planar state with a bend 430 in the linear portions 260. In some examples, the linear portions 260 extend away from a center region in pairs. The linear portions 260 can include a bend 430 disposed midway along the length of the linear portions 260. Accordingly, in an example, a pair of linear portions 260 includes respective bends 430 opposing one another, defining obtuse angles opening to one another. The linear portions 260 can include a bend 430, to aid in the rolling process. The bend 430 can be in the middle of the linear portions 260, at an equal distance from the inner switchback portion 240 and the outer switchback portion 250. Alternatively, the bend 430 can be closer to the inner switchback portion 240 than to the outer switchback portion 250, in order to shorten the inner switchback portion 240 or to increase the size of the gap 200. In another example, the bend 430 can be closer to the outer switchback portion 250 than to the inner switchback portion 250, to shorten the outer switchback portion 250 or to increase the size of the gap 200.

Figure 5A:
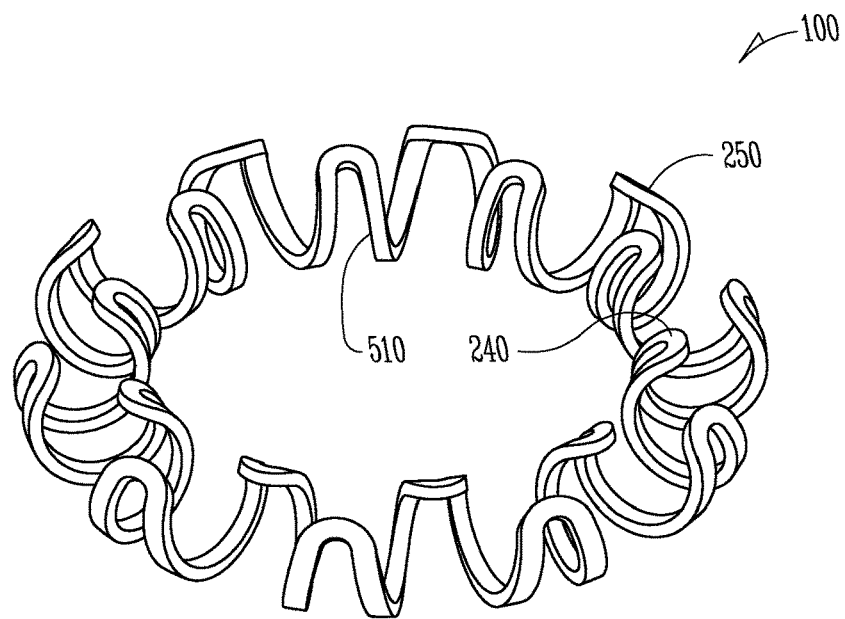
FIG. 5A is a perspective view of a spring with inner switchback portions that are shorter than outer switchback portions, according to an example.

FIG. 5A is a perspective view of an example of a spring 100, according to an example. The inner switchback portions 240 can be shorter than the outer switchback portions 250 with respect to the bend 430 or with respect to the bottom plane. This can to increase the size of the gap 200, to increase the clearance between the inner switchback portions 240 and the spring retainer 150 when the spring 100 is installed in the spring retainer 150.

Figure 5B:
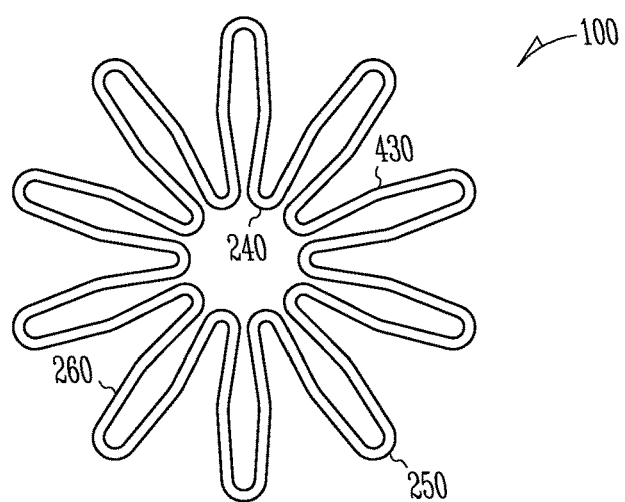
FIG. 5B shows a top view of the spring of FIG. 5A, shown in a planar state, with a bend in linear portions.

FIG. 5B shows a top view of an example of a spring 100 in a planar state with shorter inner switchback portion 240 than outer switchback portions 250. The spring 100, as shown in FIG. 5B, can be rolled, to create a spring 100, shown in FIG. 5A.

In some examples, material can be removed from the inner diameter side 510 of the spring 100, to form a relief. A relief can be created, to achieve a planar contact between the spring 100 and the lead 160. A relief can be shaped to match to the exterior shape of the lead 160. More than one of the switchback portions 240, 250 or linear portions 260 can have a relief, in order to have a uniform planar contact between the spring 100 and the lead 160, extending around the centerline 210. The plurality of reliefs can collectively define a cylindrical shape, to receive and match the exterior shape of the lead 160. In some examples, the relief can be a machined, excised, ground or melted. A relief can also be formed by compressing the spring 100 around the lead 160. A relief can also assist in the detent mechanism of the spring 100, to mechanically resist movement of the proximal end of the lead 160.

Figure 6:
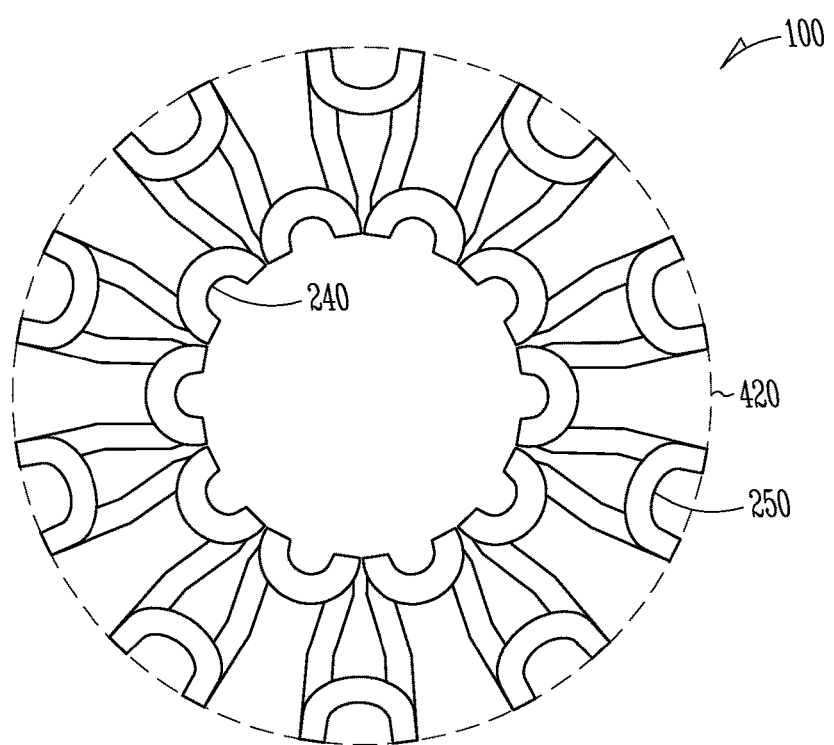
FIG. 6 shows a top view of the spring in a compressed state, according to an example.

FIG. 6 shows a top view of the spring 100 in a compressed state, according to an example. The spring 100 can be compressed, to decrease the size of the outer circumference 204 of the spring 100. The outer circumference 204 of the spring 100 can be decreased in size, to fit the spring 100 through the middle of the spring retainer 150 during installation of the spring 100 into the spring retainer 150. The spring 100 can be made of an elastically deformable material, to allow the spring 100 to return to its non-compressed state after the compressive force is removed from the spring 100. A compressive force can be removed from the spring 100, returning the spring 100 to its non-compressed state inside the spring retainer 150. In a compressed state, the outer circumference 204 of the spring 100 can be 25% smaller than the outer circumference 204 of the spring 100 in a non-compressed state. Other possibilities exist for the percent difference between the outer circumference 204 of the spring 100 in a compressed state and the outer circumference 204 of the spring 100 in a non-compressed state.

FIG. 7A shows a top view of an example of the spring 100' in a planar state, according to an example. In an example, the spring 100' can be stamped from a sheet of material. In an example, the stamped shape can be mostly flat. In an example, the stamped shape can be made up of linear components 710. In an example, the stamped shape can be symmetric across one axis. In an example, the stamped shape can be symmetric across two axes. The alternating linear components 710 can intersect creating an "X" shape, shown in FIG. 7A, to create an "X" shaped switchback portion 240, 250. The alternating linear components 270 can intersect creating a point or a "V" shape, to create a "V" shaped switchback portion 240, 250. The angles formed by the intersecting linear components 710 can be of the same degree. The angles formed by the intersecting linear components 710 can be of different degrees.

FIG. 7B shows a side view of an example of the stamped shape of FIG. 7A. The stamped shape of FIG. 7A can have an end view of a linear shape. The end view can be mostly rectangular, when the spring 100 is stamped. The end view can be mostly flat, when the spring 100' is stamped.

FIG. 8A shows a top view of an example of the spring 100' in a rolled state, according to an example. The mostly flat and linear component shown in FIG. 7A and FIG. 7B can be rolled to create a spring 100' in a rolled state, to define the gap 200. The linear components 710 can be rolled along their longest axis, to create the spring 100' in a rolled state.

FIG. 8B shows a side view of the example of FIG. 8A. The spring 100' in a rolled state can have an overall "C" shaped cross-section, when the entire spring 100' in a rolled state is viewed from one of the ends. The opening of the "C" is the gap 200 between the switchback portions 240', 250'.

FIG. 9A, FIG. 9B, and FIG. 9C are top views of an example of the spring 100, according to an example. The spring 100' in a rolled state can have its two ends connected, to define a conceptualized loop 215. The loop 215 can be circular, having a constant distance between the loop 215 and the centerline 210, as the loop extends around the centerline 210.

FIG. 10 is an example of a method of creating the spring 100. In an example, the spring 100 can be formed from material in a sheet. The sheet can be generally flat. Stamping the spring 100 from the sheet of material can define the shape of the spring 100 in a planar state. A 2-dimensional pattern may be stamped to create a spring 100 in a planar state. The stamping process can create a generally flat spring 100. The generally flat spring 100 can define a complete loop 215, such that the spring 100 does not have a defined beginning or end along the loop 215 around a centerline 210. In other words, the spring does not have a weld seam or similar grain boundary at which two portions are mechanically joined.

In instances in which the generally flat spring 100 does not create a continuous loop after stamping, connecting two ends of a generally flat spring 100 can create a continuous loop. Connecting the two ends of a generally flat spring 100 can include welding. Connecting the two ends of a generally flat spring 100 can include the use of an adhesive. Connecting the two ends of a generally flat spring 100 can include melting. The generally flat spring 100 can have a male end and female end. Connecting the two ends of a generally flat spring 100 can include connecting a male end and a female end.

In an example, the spring 100 is progressively stamped from a sheet of material that can be a carrier member 400 connecting the spring 100 to the strip of material 440 it was stamped from, to assist in locating or securing the spring 100 during the manufacturing process. The method can include rolling the switchback portions 240, 250 that zigzag around a centerline 210 to define the spring 100, to curve the switchback portions 240, 250 about a loop 215. The method can include progressively rolling the switchback portions 240, 250, to increase the efficiency of manufacturing, by simplifying tooling, reducing scrap, and decreasing cycle time, among others.

The zigzag can have inner switchbacks portions 240 and outer switchback portions 250. The method can include rolling the inner switchback portions 240 about the loop 215 away from the centerline 210. The method can include rolling the outer switchback portions 250 about the loop 215 towards the centerline 210, and towards the inner switchback portions 240, to define the gap 200. The method can include removing the carrier member 400, after the switchback portions 240, 250 are curved around a loop 215, such that only parts of the spring 100 remain. Removing the carrier member 400 can occur after one or more switchback portions 240, 250 have been rolled to curve around a loop 215. Removing the carrier member 400 can occur before the switchback portion 240, 250 are rolled to curve around a loop 215.

In an example, compressing the spring 100 can fit the spring 100 into the spring retainer 150. Compressing the spring 100 can make the outer circumference 204 of the spring 100 smaller than the inside circumference of the spring retainer 150. The outer circumference 204 of the spring 100 can be made smaller than the inside circumference of the spring retainer 150, to pass the spring 100 through the middle of the spring retainer 150. In an example, inserting the spring into the middle of the spring retainer 150, can locate the spring in the desired location for the spring 100. Removing the compressive force can allow the spring 100 to return to its uncompressed state inside the spring retainer 150. Constraining the spring 100 within the spring retainer 150 after the compressive force is removed can restrict the movement of the spring 100. The method can include inserting a lead 160 through the middle of the spring 100, along the centerline 210. The spring 100 can act as a detent for the lead 160, to secure the lead 160 to the implantable medical device 110.

FIG. 11 is an example of a method of creating the spring 100. In an example, the spring 100 can be created from material in a sheet. The sheet can be generally flat. The method can include stamping the spring 100 from the sheet of material, to define the spring 100 in a planar state. The method can include progressively stamping the spring 100 from the sheet of material, to increase manufacturing capabilities. The stamping can be a 2-dimensional pattern, to define the shape of the spring 100 in a planar state. The stamping process can result in a generally flat spring 100. The generally flat spring 100 can be mostly linear. In an example, the mostly linear generally flat spring 100 can be created by connecting linear components 710 together, by welding or with adhesive. The method can include creating the linear components 710 by cutting, stamping, or laser etching. Connecting the linear components 710 can be by welding, connecting with adhesive, or connecting with a mechanical fastener.

Rolling the linear generally flat spring 100 can curve the switchback portions 240, 250 and define the gap 200. Rolling the spring 100 can create a spring 100 with a cross section of a "C". The gap 200 defined by the inner switchback portions 240 and the outer switchback portions 250 can form the opening of the "C" cross-section.

After the spring 100 has been rolled, connecting the two ends of the rolled spring 100 can define a loop 215. The connecting of the two ends of the rolled spring 100 can be by welding, adhesive or with a male end and a female end. The gap 200 can be aligned with a plane perpendicular to the centerline 210. Compressing the spring 100 can decrease the size of the spring 100, to fit the spring 100 into the spring retainer 150. Once the spring 100 is in inside the spring retainer 150, removing the compressive force can return the spring 100 to its previous non-compressed shape.

Various Notes & Examples

Example 1 can include subject matter (such as an apparatus, a method, a means for performing acts, or a machine-readable medium including instructions that, when performed by the machine, cause the machine to perform acts) that can include or use an apparatus for use within a header of an implantable medical device. The apparatus can include a substantially annular spring, sized and shaped to be disposed in the header, the spring defining a loop extending about a central axis, the spring including a plurality of elastically deformable switchback portions that both zigzag and curve transversely about the loop to define a surface that at least partially encompasses the loop.

Example 2 can include, or can optionally be combined with the subject matter of Example 1 to optionally include the spring defining a toroid-shaped exterior.

Example 3 can include, or can optionally be combined with the subject matter of any one or more of Examples 1 or 2 to optionally include the spring defining a toroid-shaped interior void.

Example 4 can include, or can optionally be combined with the subject matter of any one or more of Examples 1 through 3 to optionally include the spring defining a gap extending from the toroid-shaped interior void through to the exterior of the toroid-shaped exterior.

Example 5 can include, or can optionally be combined with the subject matter of any one or more of Examples 1 through 4, to optionally include the gap extending around the central axis to define a loop-shaped gap.

Example 6 can include, or can optionally be combined with the subject matter of any one or more of Examples 1 through 5 to optionally include the loop-shaped gap comprising a ring-shaped gap that has a generally uniform width.

Example 7 can include, or can optionally be combined with the subject matter of any one or more of Examples 1 through 6 to optionally include, when in a planar state, one or more of the switchback portions being arc-shaped. In the example, the spring can include linear portions, when in the planar state, that extend between respective switch-backs.

Example 8 can include, or can optionally be combined with the subject matter of any one or more of Examples 1 through 7 to optionally include the loop being substantially planar. When out of the planar state, a particular one of the linear portions can be curved at least partially around a tangential axis that is tangential to the loop.

Example 9 can include subject matter (such as an apparatus, a method, a means for performing acts, or a machine-readable medium including instructions that, when performed by the machine, cause the machine to perform acts), or can optionally be combined with the subject matter of any one or more of Examples 1 through 8, to include obtaining or providing a sheet of material; forming from the material a member comprising a plurality of switchback portions that zigzag about a loop; and shaping the member such that the plurality of switchback portions are elastically deformable and zigzag and curve about the loop.

Example 10 can include, or can optionally be combined with the subject matter of any one or more of Examples 1 through 9 to optionally include the forming comprising stamping the material.

Example 11 can include, or can optionally be combined with the subject matter of any one or more of Examples 1 through 10 to optionally include the shaping including rolling.

Example 12 can include, or can optionally be combined with the subject matter of any one or more of Examples 1 through 11 to optionally include rolling that can include progressive rolling.

Example 13 can include, or can optionally be combined with the subject matter of any one or more of Examples 1 through 12 to optionally include maintaining a position of the member with respect to a fixture while rolling using a web.

Example 14 can include, or can optionally be combined with the subject matter of any one or more of Examples 1 through 13 to optionally include removing the web.

Example 15 can include, or can optionally be combined with the subject matter of any one or more of Examples 1 through 14 to optionally include compressing the member to install the member into a header of an implantable medical device.

Example 16 can include, or can optionally be combined with the subject matter of any one or more of Examples 1 through 15 to optionally include removing a compressive force to allow the member to elastically expand to be constrained against the header.

Example 17 can include subject matter (such as an apparatus, a method, a means for performing acts, or a machine-readable medium including instructions that, when performed by the machine, cause the machine to perform acts), or can optionally be combined with the subject matter of any one or more of Examples 1 through 16 to include or use an apparatus for use within a header of an implantable medical device. The apparatus can include a biocompatible annular spring sized and shaped to be disposed in the header. The spring can define a ring-shaped loop extending around a central axis. The spring can include a plurality of elastically deformable switchback portions that zigzag and curve about the loop. The spring can be formed by a process that can include obtaining or providing a sheet of material; forming from the material a member comprising a plurality of switchback portions that zigzag about a loop; and shaping the member such that the plurality of switchback portions are elastically deformable and zigzag and curve about the loop.

Example 18 can include, or can optionally be combined with the subject matter of any one or more of Examples 1 through 17 to optionally include the forming comprising stamping the material. The example can include shaping that can include rolling. The spring can be formed of biocompatible material including 35% Ni, 35% Co, 20% CR, and 10% Mo.

Example 19 can include, or can optionally be combined with the subject matter of any one or more of Examples 1 through 18 to optionally include or use the spring that can include at least one relief that can include a surface shaped to conform to a surface of a lead associated with the implantable medical device.

Example 20 can include, or can optionally be combined with the subject matter of any one or more of Examples 1 through 19 to optionally include at least one relief that can be part of a plurality of reliefs that can collectively define a cylindrical shape that can be sized to receive and conform to the lead.

Example 21 can include, or can optionally be combined with the subject matter of any one or more of Examples 1 through 20 to optionally include at least one relief that can be formed by a process that can include compressing the spring around the lead.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method comprising:
    obtaining or providing a sheet of material;
    forming from the material a member comprising a plurality of switchback portions that zigzag about a loop, wherein the forming comprises stamping the material; and
    shaping the member such that the plurality of switchback portions are elastically deformable and zigzag and curve about the loop, wherein the shaping includes rolling; and
    maintaining a position of the member with respect to a fixture while rolling using a web.

2. The method of claim 1, wherein rolling includes progressive rolling.

3. The method of claim 1, comprising removing the web.

4. The method of claim 1, comprising compressing the member to install the member into a header of an implantable medical device.

5. The method of claim 4, comprising removing a compressive force to allow the member to elastically expand to be constrained against the header.

6. The method of claim 1, A method comprising:
    obtaining or providing a sheet of material;
    forming from the material a member comprising a plurality of switchback portions that zigzag about a loop; and
    shaping the member such that the plurality of switchback portions are elastically deformable and zigzag and curve about the loop,
    wherein, shaping includes forming a spring and wherein the loop extends about a central axis and defines a horizontal plane perpendicular to the central axis, wherein shaping includes shaping the member such that a gap runs in the horizontal plane, and the gap is defined by a width between an end of the inner switchback portion and an end of the outer switchback portion, the gap dimensioned such that there is no overlap between the end of the inner switchback portion and the end of the outer switchback portion.

7. The method of claim 6, wherein the spring defines a toroid-shaped exterior.

8. The method of claim 7, wherein e spring defines a toroid-shaped interior void.

9. The method of claim 8, wherein the gap extends from the toroid-shaped interior void through to the exterior of the toroid-shaped exterior.

10. The method of claim 9, wherein the gap extends around the central axis to define a loop-shaped gap.

11. The method of claim 6, wherein when in a planar state, one or more of the switchback portions is arc-shaped, and wherein the spring includes linear portions, when in the planar state, that extend between respective switch-backs.

12. The method of claim 11, wherein when out of the planar state, a particular one of the linear portions is curved at least partially around a tangential axis that is tangential to the loop.

* * * * *